United States Patent [19]

Nardi et al.

[11]  4,275,071
[45]  Jun. 23, 1981

[54] IMIDAZOLE DERIVATIVES

[75] Inventors: Dante Nardi; Alberto Tajano; Maria J. Magistretti, all of Milan, Italy

[73] Assignee: Recordati S.A., Chiasso, Switzerland

[21] Appl. No.: 56,290

[22] Filed: Jul. 10, 1979

[30] Foreign Application Priority Data

Jul. 26, 1978 [IT] Italy .............................. 26094 A/78

[51] Int. Cl.³ .................. C07D 233/60; C07D 233/58
[52] U.S. Cl. ................................ 424/273 R; 542/400;
542/457; 542/458; 542/468; 542/470; 548/327;
548/335; 548/341; 564/337; 564/338; 564/342;
564/344; 568/328; 568/329; 568/331; 568/337;
568/744; 568/763; 568/807; 568/808
[58] Field of Search ................ 548/341, 335; 542/400,
542/458, 468, 469, 457, 470; 424/273 R

[56] References Cited

U.S. PATENT DOCUMENTS

| | | | |
|---|---|---|---|
| 3,050,520 | 8/1962 | Erner et al. | 548/335 X |
| 3,927,017 | 12/1975 | Heeres et al. | 548/335 |
| 3,954,871 | 5/1976 | Buu-Hoi et al. | 548/341 X |
| 4,006,243 | 2/1977 | Strehlke et al. | 548/335 X |
| 4,067,989 | 1/1978 | Shephard et al. | 548/341 X |
| 4,085,209 | 4/1978 | Miller et al. | 548/341 X |
| 4,104,383 | 8/1978 | Krausz | 542/470 X |
| 4,105,762 | 8/1978 | Miller et al. | 548/341 X |
| 4,110,447 | 8/1978 | Gante et al. | 548/341 X |
| 4,113,465 | 9/1978 | Shephard et al. | 548/341 X |
| 4,150,153 | 4/1979 | Walker | 548/341 X |
| 4,159,380 | 6/1979 | Hoehn | 548/341 X |

OTHER PUBLICATIONS

*Chemical Abstracts,* 84:104576t (1976) [Cooper, G. et al., *ORG. Mass Spectrom.,* 1975, 10, 885–895].
*Chemical Abstracts,* 88:152617m (1978) [Timmler, H., et al., German Ols 2,628,420, 1/5/78].

*Primary Examiner*—Richard A. Schwartz

*Attorney, Agent, or Firm*—Stevens, Davis, Miller & Mosher

[57] ABSTRACT

Imidazole derivatives of the formula I and pharmaceutically acceptable acid addition salts thereof are provided:

$$R_4-\underset{\underset{R_3}{|}}{\overset{\overset{R_2}{|}}{C}}-\underset{\underset{R_1}{|}}{\overset{\overset{R}{|}}{C}}-(CH_2)_n-N\diagup\diagdown \begin{matrix}HC=N\\ \phantom{xx}|\\ \phantom{xxx}CH\\ C\\ H\end{matrix} \qquad I$$

In the formula, $R_4$ 1- or 2-naphthyl, optionally substituted with Cl, Br, or I; 1,2,3,4-tetrahydro-6-naphthyl; 3-duryl, optionally 6-substituted by Cl, Br, I, $NO_2$, $CH_3$ or benzyl; mesityl, phenyl 2-, 3- or 4-substituted by OH, $NH_2$, $NO_2$, $CH_3CONH$, phenyl, phenoxy, cyclohexyl, phenylthio, benzylthio, $C_1$–$C_6$ alkyl or $C_1C_6$ alkylthio; 4-bibenzylyl; 3,4-dihydroxyphenyl, n=0, 1 or 2 and (a) R=H, alkyl having 1 to 6 carbon atoms or phenyl $R_1$=H, alkyl having 1 to 6 carbon atoms or phenyl one of $R_2$ and $R_3$=H the other of $R_2$ and $R_3$=H, OH, benzoyloxy, $C_2$–$C_7$ alkanoyloxy, N-($C_1$–$C_6$ alkyl)-carbamoyloxy, N,N-[di-($C_1C_6$)alkyl]-carbamoyloxy, but if $R_2$=$R_3$=H then R=$R_1$=H, or (b) R=H, $C_1$–$C_6$ alkyl, phenyl $R_1$=H, $C_1$–$C_6$ alkyl, phenyl $R_2$+$R_3$=O, or $$-\underset{\underset{R_3}{|}}{\overset{\overset{R_2}{|}}{C}}-\underset{\underset{R_1}{|}}{\overset{\overset{R}{|}}{C}}-=-CH=CH-. \qquad (c)$$

The compounds of formula I are anti-convulsivants.

19 Claims, No Drawings

IMIDAZOLE DERIVATIVES

This invention relates to imidazole derivatives useful in therapy as anticonvulsant agents, to processes for the preparation of such derivatives and to pharmaceutical compositions containing them.

The invention provides imidazole derivates of the general formula

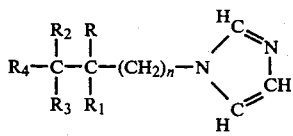

wherein $R_4$ represents a 1,2,3,4-tetrahydro-6-naphthyl group, a 3-duryl group, a 6-chloro-, 6-bromo-, 6-iodo-, 6-nitro-, 6-benzyl- or 6-methyl-3-duryl group, a 1- or 2-naphthyl group, a chloro-, bromo- or iodo-substituted 1- or 2-naphthyl group, a mesityl group, a phenyl group substituted in the 2-, 3- or 4-position by an alkyl group having from 1 to 6 carbon atoms, by an alkylthio group having from 1 to 6 carbon atoms or by a hydroxy, amino, nitro, acetamido, phenyl, phenoxy, cyclohexyl, phenylthio or benzylthio group, a 4-bibenzyl group or a 3,4-dihydroxy-phenyl group, n is 0, 1 or 2, and (a) each of R and $R_1$, which may be the same or different represents a hydrogen atom, an alkyl group having from 1 to 6 carbon atoms or a phenyl group, one of $R_2$ and $R_3$ represents a hydrogen atom, and the other of $R_2$ and $R_3$ represents a hydrogen atom, a hydroxy group, a benzoyloxy group, an alkanoyloxy group having from 2 to 7 carbon atoms, an N-alkylcarbamoyloxy group in which the alkyl group has from 1 to 6 carbon atoms or an N,N-dialkylcarbamoyloxy group in which each alkyl group has from 1 to 6 carbon atoms, with the proviso that if $R_2$ and $R_3$ both represent hydrogen atoms then R and $R_1$ both represent hydrogen atoms, or (b) R, $R_1$ and $R_4$ are as defined in (a) and $R_2$ and $R_3$ together represent an oxygen atom, or (c) $R_4$ is the same as in (a) and

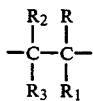

represents a vinylene group, and
pharmaceutically acceptable acid addition salts of (a), (b) and (c).

For convenience, the imidazole derivatives of the general formula I wherein R, $R_1$, $R_2$ and $R_3$ have the meanings assigned to them in alternative (a) of the above definition are hereinafter called compounds (Ia); those in which R, $R_1$, $R_2$ and $R_3$ have the meanings assigned to them in alternative (b) of the above definition are hereinafter called compounds (Ib); and those in which R, $R_1$, $R_2$ and $R_3$ have the meanings assigned to them in alternative (c) of the above definition are hereinafter called compounds (Ic). The compounds (Ia) in which one of $R_2$ and $R_3$ represents a hydrogen atom and the other a hydroxy group are hereinafter called compounds (Iai); those in which $R_2$ and $R_3$ both represent hydrogen atoms are called compounds (Iaii); and the compounds (Ia) that are neither compounds (Iai) nor compounds (Iaii) are called compounds (Iaiii).

The compounds (Ib) may be prepared by either of two methods, both of which are within the scope of the invention. The first method comprises reacting a compound of the general formula II (see the reaction scheme herein) in which R and $R_1$ have the meanings assigned in alternative (a) of the above definition, $R_4$ and n have the meanings assigned in the above definition and Y represents a chlorine or bromine atom with imidazole or a salt thereof in a solvent such as, for example, dimethylformamide or dichloroethane; the reaction temperature is preferably ambient temperature. The second method comprises reacting a compound II with dimethylamine to obtain a compound of the general formula III (see reaction scheme) in which R, $R_1$, $R_4$ and n are as defined for compounds II, and reacting the compound of formula III with imidazole or a salt thereof. The reaction with imidazole or a salt thereof is preferably carried out at ambient temperature.

The compounds (Ib) in which n=1 may additionally be prepared by a third method, also within the scope of the invention, which comprises reacting a compound of the general formula V (in the reaction scheme) in which R, $R_1$ and $R_4$ are as defined for compounds II with formaldehyde and dimethylamine under Mannich Reaction conditions to obtain a compound of formula III in which n=1, and reacting the latter with imidazole or a salt thereof. The reaction with imidazole or a salt thereof is preferably carried out at ambient temperature.

The compounds (Iai) may be prepared by two methods, both of which are within the scope of the invention. The first comprises reducing a compound (Ib) with sodium borohydride in the presence of an alcohol. The alcohol is preferably methanol. The reaction may be performed at ambient temperature and for a period of from 1 to 4 hours. The second comprises reducing a compound II with sodium borohydride in the presence of an alcohol and condensing the resultant compound of the general formula IV wherein R, $R_1$, $R_4$, Y and n are as defined for compounds II with imidazole or a salt thereof. The reduction may be performed at ambient temperature for a period of from 1 to 4 hours and a suitable alcohol is methanol or the like. The condensation may be performed at ambient temperature.

The compounds (Iaiii) may be prepared by a process according to the invention comprising esterifying a compound (Iai) with a chloride or anhydride of benzoic acid, an alkanoic acid having from 2 to 7 carbon atoms, an N-alkylcarbamic acid in which the alkyl group has from 1 to 6 carbon atoms or an N,N-dialkylcarbamic acid in which each alkyl group has from 1 to 6 carbon atoms. The esterification may be carried out at ambient temperature.

The compounds (Ic) may be prepared according to the invention by refluxing in acidic conditions a compound (Iai) in which both R and $R_1$ represent hydrogen atoms. The hydroxy group $R_2$ or $R_3$ and one of the hydrogen atoms R and $R_1$ are eliminated as water.

Still another process according to the invention enables compounds (Iaii) to be obtained, and comprises catalytically hydrogenating a compound (Ic).

These reactions are summarized in the following reaction scheme:

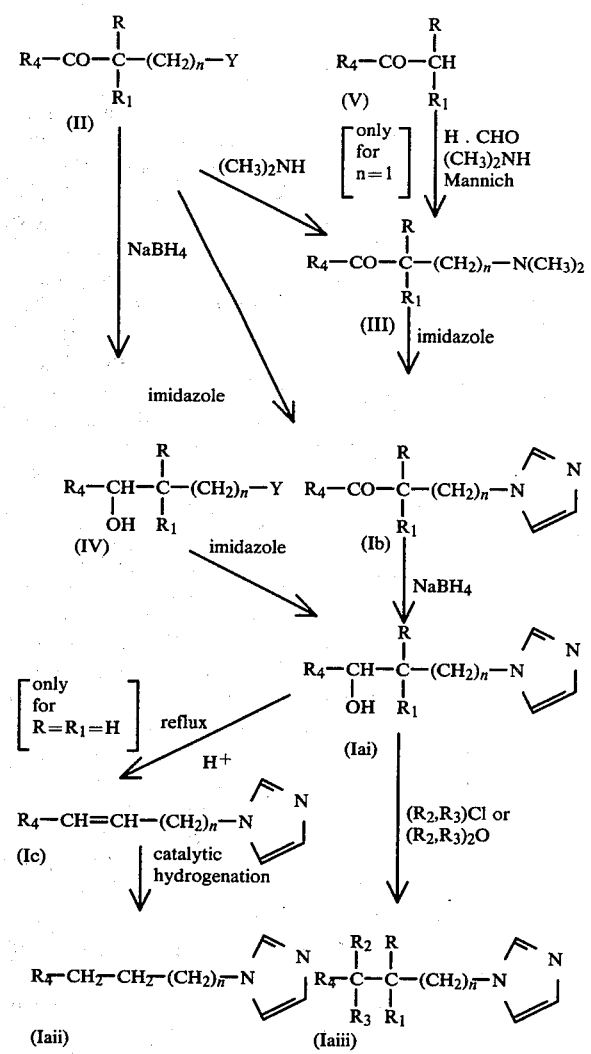

The compounds (Ia), (Ib) and (Ic) may be converted in the usual manner into their pharmaceutically acceptable acid addition salts. Acids which may be employed are both inorganic and organic, and include hydrochloric, sulphuric, nitric, phosphoric, p-toluenesulphonic, oxalic, acetic, citric, propionic, maleic, cinnamic, benzoic and methanesulphonic acids.

PHARMACOLOGY

The compounds of the invention and their salts show substantial anticonvulsant activity, coupled with low toxicity.

The anticonvulsant activity has been evaluated in the mouse with the maximum electroshock seizure test (MES) and with the subcutaneous pentylenetetrazol (Metrazol) seizure threshold test (MET), using diphenylidantoin and phenobarbital as reference substances. Even if the anticonvulsant activity of the novel imidazole derivatives was similar to or lower than the activity of the reference substances, the compounds of the invention being more soluble in water show a more regular absorption. This involves a lower absorption variation among subjects, unlike mainly diphenyl idantoin. The new compounds possess moreover a toxicity which is up to 10 to 12 times lower than that of the reference substances, and this makes the compounds extremely advantageous over diphenylidantoin and phenobarbital. MES was performed according to the method described by Swinyard et al, J. Pharmacol. exp. ther., 106, 319, 1952. The compounds of the invention have beeen solubilized in a 10% gum arabic solution and administered intraperitoneally or per os to the mice. Groups of ten animals each, albino race, both male and female, weighing 25–30 grams, have been used. Electroshock seizures have been elicited with a 60 Hz alternating current (for 0.2 sec at 25 mA). Electroshock was carried out 30 or 60 minutes after administration of the drug. This stimulus produces in normal mice, that is in mice to which no drug has been administered, a maximum seizure. It consists of a short period of initial tonic flexion and a prolonged period of hind limb tonic extension followed by terminal conus. The seisure lasts about 22 sec. Abolition of the hind limb tonic extensor component of the seizure is defined as protection and indicates anticonvulsant activity in the test compound.

In Table I, the effective doses 50 ($ED_{50}$) of the compounds administered i.p. and os, are given.

As to MET, it is known that pentylene-tetrazol (metrazol) administered subcutaneously to mice in a loose fold of skin on the back of the neck, produces seizures. Such seizures are produced in at least 97% of normal mice. The compounds to be tested have been administered to the mice as stated for MES. Pentylenetetrazol in a dose of 130 mg/Kg was injected in mice 30–60 minutes respectively after intraperitoneal and oral administration of the drug. The animals were observed for 60 minutes. Failure to observe even a threshold seizure is defined as protection. The results are reported in Table II. In the same table the $LD_{50}$ values (lethal dose 50), evaluated in the mouse both I.p. and per os, are given. All the prepared compounds exhibit a substantial anticonvulsant activity and a low toxicity. Those listed in the table are only the most indicative and, therefore, they do not exclude a priori the activity of the others.

The new imidazole derivatives can be used in the form of pharmaceutical preparations containing an amount of said compounds or salts thereof in conjunction with any suitable organic or inorganic liquid or solid carrier, such as water, gelatin, lactose, starch, magnesium stearate, talc, vegetable oils, gums, polyalkylene glycols and the like. The compositions are formulated by conventional methods and may be in any conventional pharmaceutical form, such as suspensions, emulsions, injectables, powders, granules, capsules, tablets and pellets.

They may be sterilized for parenteral administration and/or may contain additives such as conventional excipients, preserving, stabilizing, dispersing, wetting or emulsifying agents, fillers, buffers, bacteriostats, bactericidal agents, preservatives or coloring agents. In such pharmaceutical formulations, the concentration of the active ingredient may vary depending on the form the composition takes, but is generally from between 50 mg to 700 mg.

In Table I, the compounds have been indicated by numbers which refer to the Examples.

TABLE I

| COMPOUND | LD$_{50}$ mg/Kg i.p. | LD$_{50}$ mg/Kg os | ED$_{50}$ mg/Kg - MES i.p. | ED$_{50}$ mg/Kg - MES os | ED$_{50}$ mg/kg - MET i.p. | ED$_{50}$ mg/kg - MET os |
|---|---|---|---|---|---|---|
| 15/1803 | >3.000 | 2.100 | 66 | 92 | 18 | 32 |
| 1341 | 1.550 | 2.400 | 54 | 76 | 28 | 10 |
| 1488 | >3.000 | 1.870 | 30 | 34 | 25 | 37 |
| 1490 | 360 | 1.150 | 60 | 36 | 15 | 30 |
| 1532 | 300 | 1.550 | 11 | 37 | 11 | 17 |
| 1585 | >3.000 | 2.100 | 25 | 100 | 25 | 25 |
| 1323 | 420 | 1.170 | 18 | 33 | 19 | 28 |
| 1518 | >3.000 | 1.800 | 13 | 45 | 23 | 50 |
| 1517 | >3.000 | >3.000 | 80 | 80 | 150 | 150 |
| 1457 | >3.000 | 3.000 | 180 | 190 | 90 | 57 |
| 1429 | >3.000 | >3.000 | 75 | 54 | 100 | 52 |
| 1534 | 490 | 2.700 | 50 | 60 | 25 | 27 |
| 1342 | 1.150 | >3.000 | 25 | 25 | 25 | 20 |
| 1492 | 420 | 2.400 | 24 | 27 | 10 | 14 |
| 15/1533 | >3.000 | >3.000 | 10 | 12 | 9 | 10 |
| 1455 | 420 | >3.000 | 15 | 31 | 19 | 22 |
| 1540 | >3.000 | 3.000 | 155 | 150 | 39 | 150 |
| 1541 | >3.000 | 1.150 | 50 | 190 | 23 | 135 |
| 1516 | 655 | 1.800 | 46 | 57 | 13 | 35 |
| 1515 | >3.000 | >3.000 | 300 | 150 | 150 | 75 |
| 1575 | >3.000 | 1.300 | 66 | 135 | 27 | 62 |
| 1598 | >3.000 | 3.000 | 185 | 145 | 69 | 80 |
| Phenobarbital | 242 | 245 | 14 | 18 | 9 | 10 |
| Diphenylidantoin | 196 | 262 | 6 | 10 | 6 | 5 |

The invention is illustrated by Examples Nos. 10 to 23 of the following Examples, Examples 1 to 9 describing the preparation of certain novel starting materials.

EXAMPLE 1

6-bromo-3-chloroacetyl-durene (II: R and R$_1$ are H, R$_4$ is 6-bromo-3-duryl, n=O, Y=Cl)

To a suspension of 6.66 g of anhydrous aluminium trichloride in 30 ml of anhydrous chloroform, stirred at O/+5° C., 5.64 g of chloroacetyl chloride were added dropwise. The mixture so obtained was stirred until a clear solution was formed. Maintaining the temperature at O/+5° C., a solution of 10.65 g of 3-bromo-durene in 30 ml of chloroform was then added. When the addition was complete, the temperature was brought to 20°–25° C.; then the mixture was heated for two hours at 40°–45° C. At the end of the reaction, the mixture was poured in ice/hydrochloric acid and extracted with chloroform. A solution was obtained, which was washed with water to neutrality, dried on calcium chloride and evaporated to dryness. The crude product thus obtained was purified by silica gel column chromatography, using at first as eluant petroleum ether, then a mixture of petroleum ether and benzene.

The 6-bromo-3-chloroacetyl-durene was crystallized from isopropanol, giving 8.4 g of white product, melting at 127°–128° C. Yield 58%.

| Analysis for C$_{12}$H$_{14}$BrClO | | | | |
|---|---|---|---|---|
| | C % | H % | Cl % | Br % |
| Calculated | 49.77 | 4.87 | 12.24 | 27.59 |
| Found | 49.56 | 4.89 | 11.96 | 27.30 |

EXAMPLE 2

6-chloro-3-chloroacetyl-durene (II: R and R$_1$ are H, R$_4$ is 6-chloro-3-duryl, n=O, Y=Cl)

Example 1 was repeated except 8.43 g of 3-chlorodurene was used, after crystallization from ethanol. 7.3 g of 6-chloro-3-chloroacetyl-durene was obtained. M.P. 94°–96° C.

EXAMPLE 3

3-(2'-bromo-propionyl)-durene (II: R is CH$_3$, R$_1$ is H, R$_4$ is 3-duryl, n is O, Y is Br)

Example 1 was repeated except a mixture of 220 ml chloroform, 32 g of aluminium trichloride, 26.2 ml of 2-bromopropionyl bromide and 26.8 g of durene was used as the starting mixture. 42 g of the title compound were obtained. M.P. 84°–86° C. The product was purified by distillation and crystallized from ethanol.

EXAMPLE 4

3-Chloroacetyl-durene (II: R and R$_1$ are H, R$_4$ is 3-duryl, n=O, Y=Cl)

Example 1 was repeated but 1.33 g of aluminium trichloride, 1.13 g of chloroacetyl chloride and 1.34 g of durene were employed. 1.78 g of 3-chloroacetyl-durene were obtained, melting point 65.5°=66° C. The product was purified by distillation (bp 113°–117° C.)/0.4 mmHg) and crystallized from ethanol. Similarly, 3-bromoacetyl-durene, melting 53°–54° C. was obtained.

EXAMPLE 5

3-(2'bromo-2'-methyl-propionyl)-durene (II: R and R$_1$ are CH$_3$, R$_4$ is 3duryl, n=O, Y=Br)

Example 1 was repeated except 16 g of aluminium trichloride, 110 ml of chloroform, 28.72 g of 2-bromo-2-methyl propionyl bromide and 13.42 g of durene were used. 19.1 g of the title compound were obtained. The compound was crystallized from ethanol, M.P. 108°–110° C.

EXAMPLE 6

1-chloroacetyl-4-chclohexyl-benzene (II: R and R$_1$ are H, R$_4$ is p-cyclohexyl-phenyl, n=O, Y=Cl)

A mixture of 16 g of p-cyclohexyl-benzene and 11.2 g of chloroacetyl chloride was added dropwise to a mixture containing 13.3 g of aluminium trichloride and 60 ml of carbon disulphide, maintaining the temperature at 10°–15° C. The reaction was run for 6 hours, then allowed to stand at room temperature for 12 hours. The mixture was poured in ice/hydrochloric acid and extracted with dichloromethane. The extract was washed, dried and the solvent evaporated off. After distillation, the fraction boiling at 140°–150° C./0.6 mmHg was collected. The crude 1-chloroacetyl-4-cyclohexyl-benzene was crystallized from ethanol/water to give 18 g of product melting at 47°–49° C. Yield 75%

| Analysis for $C_{14}H_{17}ClO$ | | | |
|---|---|---|---|
| | C % | H % | Cl % |
| Calculated | 71.03 | 7.24 | 14.98 |
| Found | 71.23 | 7.15 | 14.76 |

EXAMPLE 7

4-[3″-(N,N-dimethylamino)-propionyl]-bibenzyl hydrochloride (III: R and $R_1$ are H, $R_4$ is 4-bibenzylyl, n=1)

To a solution of 2.43 g of dimethylamine hydrochloride in 2.25 g of 40% formaldehyde, 3 ml of acetic anhydride were added. The mixture so obtained was stirred at room temperature for 30 minutes. After heating at 120° C., a boiling solution of 6.72 g of 4-acetyl-bibenzyl in 4 ml of acetic anhydride was added. The mixture was refluxed for 1 hour and then evaporated to dryness in vacuo. The residue was treated with water and washed with diethyl ether. The aqueous layer was made alkaline and the title compound precipitated as free base.

The product was transformed into its hydrochloride by treatment with hydrogen chloride in ethanol and purified by crystallization from isopropanol. Yield 6.65 g (70%). M.P. 145°–147° C.

| Analysis for $C_{19}H_{23}NO \cdot HCl$ | | | | |
|---|---|---|---|---|
| | C % | H % | N % | Cl % |
| Calculated | 71.80 | 7.61 | 4.40 | 11.15 |
| Found | 71.96 | 7.59 | 4.48 | 11.36 |

EXAMPLE 8

4-[2″-(N,N-dimethylaminomethyl)-propionyl]-biphenyl (III: R=$CH_3$, $R_1$=H, $R_4$=4-biphenylyl, n=1)

A mixture consisting of 16.3 g of dimethylamine hydrochloride, 15 ml of 40% formaldehyde and 20 ml of acetic anhydride, was stirred for 30 minutes at room temperature and then heated to boiling. A boiling solution of 42 g of 4-propionyl-biphenyl in 30 ml of acetic anhydride was then slowly added. At the end of the reaction, water and then hydrochloric acid were added until the solution was neutral. The whole was then extracted with diethyl ether. The mixture was cooled at 5°–10° C., 20% sodium carbonate was added, then it was filtered off and the residue was dried, M.P. 59° C.

The base thus obtained, dissolved in methanol, was transformed into its hydrochloride by treatment with hydrogen chloride/ethanol and, adding diethyl ether, it crystallized. The product was recrystallized from isopropanol. Yield 39.5 g (65%) M.P. 187° C.

| Analysis for $C_{18}H_{21}NO \cdot HCl$ | | | | |
|---|---|---|---|---|
| | C % | H % | N % | Cl % |
| Calculated | 71.16 | 7.30 | 4.61 | 11.67 |
| Found | 70.96 | 7.43 | 4.57 | 11.31 |

EXAMPLE 9

2-bromoacetyl-biphenyl (II: R and $R_1$ are H, $R_4$ is 2-biphenylyl, n=0, Y=Br)

A solution of 2.17 g of 2-phenyl-benzoyl chloride in 7 ml of anhydrous benzene was dropped at 15°–20° C. into a suspension of cadmium dimethyl, prepared from 0.0125 mol of methyl magnesium iodide, in 7 ml of anhydrous benzene stirred in nitrogen atmosphere. When the addition was complete, the mixture was refluxed for 4 hours. At the end of the reaction, the whole was poured into ice/hydrochloric acid and extracted with benzene. The benzenic solution was washed with sodium bicarbonate and water until neutral, dried over anhydrous sodium sulphate and evaporated to dryness in vacuo. After distillation, 1.51 g of 2-acetyl-biphenyl, bp 104=105° C./0.2 mm Hg, were obtained.

To a solution of 1.86 g of 2-acetyl-biphenyl in 10 ml of anhydrous chloroform, a solution of 1.29 g of bromine in 1.5 ml of anhydrous chloroform was added at 15°–20° C. When the addition was complete, the solution was stirred for 15 minutes, then poured into water. The chloroformic solution was washed with sodium bicarbonate and water, dried over calcium chloride and evaporated to dryness. 2.54 g of 2-bromoacetyl-biphenyl were obtained; the product could be used for reaction with imidazole without further purification.

EXAMPLE 10

4-(N-imidazolyl-acetyl)-biphenyl (15/1341)

(Ib: n=0, R and $R_1$ are H, $R_4$ is 4-biphenylyl)

To a suspension of 6.81 g of imidazole in 40 ml of 1,2-dichloroethane, stirred at room temperature, were added slowly 4.6 g of 4-bromoacetyl-biphenyl. The clear solution thus obtained was maintained at room temperature overnight, then the solvent was evaporated off at a pressure below atmospheric and the residue washed with 20 ml of water and crystallized from toluene. 4.67 g of the title compound were obtained; M.P. 195°–8° C.

| Analysis for $C_{17}H_{14}N_2O$ | | | |
|---|---|---|---|
| | C % | H % | N % |
| Calculated | 77.84 | 5.38 | 10.68 |
| Found | 78.01 | 5.51 | 10.51 |

Operating as described above, but starting respectively from 4-(3″-chloro-propionyl)-biphenyl, 4-(2″-chloro-propionyl)biphenyl, 1-chloroacetyl-4-cyclohexyl-benzene and 4-(3″-chloropropionyl)-bibenzyl, the following compounds have been obtained:

4-[3″-(N-imidazolyl)-propionyl]-biphenyl (15/1490)

(Ib: n=1, R and $R_1$ are H, $R_4$ is 4-biphenylyl) M.P. 149°–151° C. 4-[2″-methyl-2″-(N-imidazolyl)-propionyl]-biphenyl (15/1488)

(Ib: n=0, R and $R_1$ are $CH_3$, $R_4$ is 4, biphenylyl, M.P. 167°–8° C.

1-(N-imidazolyl-acetyl)-4-cyclohexyl-benzene (15/1503)

(Ib: n=0, R and R$_1$ are H, R$_4$ is 4-cyclohexyl-phenyl) M.P. 132°-3° C.

4-[3″-N-imidazolyl)-propionyl]-bibenzyl (15/1585)

(Ib: n=1, R and R$_1$ are H, R$_4$ is 4,bibenzylyl) M.P. 104°-5° C.

EXAMPLE 11

3-(N-imidazolyl-acetyl)-biphenyl (15/1409)

(Ib: n=0, R and R$_1$ are H, R$_4$ is 3-biphenylyl)

Operating as described in Example 10, but starting from 2.75 g of 3-bromoacetyl-biphenyl, 1.06 g of the title product, melting at 128°-9° C. were obtained. The compound was purified by silica gel column chromatography, using dioxan as eluant, and subsequently crystallized from benzene. Yield 40%.

EXAMPLE 12

1-(N-imidazolyl-acetyl)-naphthalene hydrochloride (15/1422)

(Ib: n=0, R and R$_1$ are H, R$_4$ is 1-naphthyl)

To a mixture containing 2.72 g of imidazole in 2 ml of dimethylformamide, cooled at 5° C., a mixture containing 2.48 g of 1-bromoacetyl-naphthalene in 1 ml of dimethylformamide was added. After 3 hours at 5° C., the mixture was poured into water and then allowed to stand until an oily product was obtained. Hydrochloric acid was added, then diethyl ether was added and the extract was made alkaline with sodium hydroxide. The whole was extracted again with ethyl acetate, washed with water and dried over anhydrous sodium sulphate. The oily product thus formed was purified by silica gel column chromatography using acetone as eluant. 1.44 g of the title compound were obtained and then transformed into its hydrochloride by treating the free base in ethanol with gaseous hydrogen chloride. The salt melts at 218° C., yield 55%.

| Analysis for C$_{15}$H$_{12}$N$_2$O . HCl | | | | |
|---|---|---|---|---|
| | C % | H % | N % | Cl % |
| Calculated | 66.06 | 4.80 | 10.27 | 13.00 |
| Found | 65.72 | 4.78 | 10.12 | 12.92 |

EXAMPLE 13

4-(N-imidazolyl-acetyl)-bibenzyl (15/1532)

(Ib: n=0, R and R$_1$ are H, R$_4$ is 4-bibenzylyl)

To a solution containing 3.4 g of imidazole in 5 ml of dimethylformamide, stirred at 0/+5° C., 2.58 g of 4-chloroacetyl-bibenzyl were slowly added. The reaction mixture was stirred for few minutes, then allowed to stand and then poured into water. The product thus formed was filtered off, purified by silica gel column chromatography (eluant: benzene/acetone) and then crystallized from ethyl acetate to give 2.24 g of the title compound melting at 134°-6° C. Yield 77%.

| Analysis for C$_{19}$H$_{18}$N$_2$O | | | |
|---|---|---|---|
| | C % | H % | N % |
| Calculated | 78.59 | 6.25 | 9.65 |
| Found | 78.60 | 6.48 | 9.55 |

EXAMPLE 4

4-[2″-N-imidazolyl)-propionyl]-biphenyl (15/1427)

(Ib: n=0, R=CH$_3$, R$_1$=H, R$_4$=4-biphenylyl)

Example 12 was repeated except 3.4 g of imidazole and 2.89 g of 4-(3″-bromopropionyl)-biphenyl were used. 1.55 g of the title compound, as free base, were obtained. M.P. 113°-121° C.

EXAMPLE 15

3-(N-imidazolyl-acetyl)-durene (15/1323)

(Ib: n=0, R and R$_1$ are H, R$_4$ is 3-duryl)

A mixture containing 2.55 g of 3-bromoacetyl-durene, prepared as described in Example 4, 3 ml of dimethylformamide and 3.40 g of imidazole, was stirred for 8 hours at 80° C. At the end of the reaction, the mixture was cooled to room temperature and 25 ml of water were added. The precipitate thus obtained was filtered off, dried and crystallized from benzene to give 1.5 g of the title compound. M.P. 176°-8° C., yield 62%.

| Analysis for C$_{15}$H$_{18}$N$_2$O | | | |
|---|---|---|---|
| | C % | H % | N % |
| Calculated | 74.35 | 7.49 | 11.56 |
| Found | 74.46 | 7.66 | 11.65 |

Operating as described above, but substituting for the 3-bromoacetyl-durene, 6-methyl-, 6-bromo-, 6-chloro- and 6-nitro-3-bromoacetyl-durene, the following compounds have been synthesized:

3-(N-imidazolyl-acetyl)-6-methyl-durene (15/1518)

(Ib: n=0, R and R$_1$ are H, R$_4$ is 6-methyl-3-duryl) M.P. 187°-9° C.

3-(N-imidazolyl-acetyl)-6-bromo-durene (15/1457)

Ib: n=0, R and R$_1$ are H, R$_4$=6-bromo- 3-duryl) M.P. 201° C. with decomposition 3-(N-imidazolyl-acetyl)-6-chloro-durene (15/1517)

(Ib: n=0, R and R$_1$ are H, R$_4$ is 6-chloro-3-duryl) M.P. 202°-9° C.

3-(N-imidazolyl-acetyl)-6-nitro-durene (15/1429)

(Ib: n=0, R and R$_1$ are H, R$_4$ is 6-nitro-3-duryl) m.p. 190°-2° C.

EXAMPLE 16

4-[1″-hydroxy-2″-(N-imidazolyl)-ethyl]-biphenyl (15/1342)

(Iai: n=0, R and R$_1$ are H, R$_4$ is 4-biphenylyl)

To a stirred suspension containing 2.62 g of 4-(N-imidazolyl-acetyl)-biphenyl, prepared as described in Example 10, in 26 ml of methanol, 0.38 g of sodium borohydride were added to that the temperature never rose above 35° C. The mixture was maintained at room temperature for 2 hours, then refluxed for 1 hour. Hydrochloric acid (10 ml), and 30 ml of water were added, and the whole was then stirred at room temperature for 3 hours. The precipitate thus obtained was filtered off, washed with water and crystallized from dioxan to give 2.19 g (83%) of the title compound, M.P. 183°-4° C.

| Analysis for C$_{17}$H$_{16}$N$_2$O | | | |
|---|---|---|---|
| | C % | H % | N % |
| Calculated | 77.25 | 6.10 | 10.60 |
| Found | 77.15 | 5.99 | 10.69 |

The title compound was also prepared by reacting, in formamide, imidazole or its sodium salt with 4-(1″-hydroxy-2″-chloro-ethyl)diphenyl, prepared according to J. Sarn et al, J. Pharm. Sci., 57, 564, 1968.

Operating as above, but starting from 1-(N-imidazolylacetyl)-4-cyclohexyl-benzene, obtained as described in Example 10, 1-[1′-hydroxy-2′-(N-imidazolyl)-ethyl]-4-cyclohexyl-benzene (15/1534) (Iai: n=0, R and R$_1$ are H, R$_4$ is 4-cyclohexyl-phenyl) (M.P. 202°–3° C.) was prepared.

EXAMPLE 17

4-[1″-hydroxy-2″-(N-imidazolyl)-ethyl]-bibenzyl (15/1533)

(Iai: n=0, R and R$_1$ are H, R$_4$ is 4-bibenzylyl)
To a solution of 2.90 g of 4-(n-imidazolyl-acetyl)-bibenzyl, prepared as described in Example 13, in 20 ml of methanol, 0.38 g of sodium borohydride as added at room temperature.

The mixture was refluxed for 2 hours, then the solvent was evaporated off in vacuo and water added to the residue. The product, collected by filtration, was crystallized from ethanol to give 2.7 g of the title compound M.P. 165°–6° C.

| Analysis for C$_{19}$H$_{20}$N$_2$O | C % | H % | N % |
|---|---|---|---|
| Calculated | 78.05 | 6.90 | 9.58 |
| Found | 78.34 | 6.91 | 9.56 |

EXAMPLE 18

Operating as described in Examples 16 and 17, but employing respectively 3-(N-imidazolyl-acetyl)-6-methyl-durene and 3-(N-imidazolyl-acetyl)-6-chloro-durene, prepared as described in example 15, the following were synthesized:

3-[1′-hydroxy-2′-(N-imidazolyl)-ethyl]-6-methyl-durene (15/1516)

(Iai: n=0, R and R$_1$ are H, R$_4$ is 6-methyl-3-duryl) M.P. 221°–2° C.

3-[1′-hydroxy-2′-(N-imidazolyl)-ethyl]-6-chloro-durene (15/1515)

(Iai: n=0, R and R$_1$ are H, R$_4$ is 6-chloro-3-duryl) M.P. 225°–6° C.

EXAMPLE 19

4-[1″-(N,N-diethyl-carbamoyloxy)-2″-(N-imidazolyl)-ethyl]-biphenyl hydrochloride (15/1589)

(Iaii: n=0, R=R$_1$=R$_2$=H, R$_3$=N,N-diethylcarbamoyloxy, R$_4$=4-biphenyl)

To 10.56 g of 4-[1″-hydroxy-2″-(N-imidazolyl)-ethyl]-biphenyl, prepared as described in Example 16, in 100 ml of dimethylformamide, 2.30 g of sodium borohydride in 50:% oily suspension were slowly added. The mixture was stirred at 25°–30° C. for 1 hour, then 5.44 g of N,N-diethylcarbamoyl chloride were added. The mixture was refluxed for 5 hours, then poured into water and extracted with diethyl ether. The product obtained after evaporation of the solvent was purified by silica gel column chromatography, using benzene/acetone (3:2) as eluant. The desired compound (11 g) was transformed into its hydrochloride by adding hydrogen chloride in isopropanol. M.P. 215°–6° C., yield 76%. Operating as above, but using benzoyl chloride, 4-[1″-benzoyloxy-2″-(N-imidazolyl)-ethyl]-biphenyl was prepared and isolated as its benzoate (15/1575).

(Iaiii: n=0, R, R$_1$ and R$_2$ are H, R$_3$ is benzoyloxy, R$_4$ is 4-biphenylyl) M.P. 144°–5° C.

EXAMPLE 20

4-[1″-propionyloxy-2″-(N-imidazolyl)-ethyl]-biphenyl (15/1574)

(Iaiii: n=0, R, R$_1$ and R$_2$ are H, R$_3$ is propionyloxy, R$_4$ is 4-biphenylyl)

A mixture containing 13.2 g of 4-[1″'-hydroxy-2″-(N-imidazolyl)-ethyl]-biphenyl, prepared as described in Example 16, 50 ml pyridine and 26 ml of propionic anhydride was heated at 80° C. for 2 hours. At the end of heating, the mixture was cooled, poured into water and, after 4–5 hours standing, the water was decanted off. The oily residue, to which water was added, was then extracted with diethyl ether. The extract was washed twice with 5% sodium bicarbonate and once with water then dried over anydrous sodium sulphate. The solvent was evaporated off and the residue was crystallized from cyclohexane to give 5.5 g of the title compound. M.P. 90°–92° C., yield 34%.

| Analysis for C$_{20}$H$_{20}$N$_2$O$_2$ | C % | H % | N % |
|---|---|---|---|
| Calculated | 74.97 | 6.29 | 8.74 |
| Found | 74.84 | 6.57 | 8.93 |

Operating as above but employing respectively acetic anhydride and butyric anhydride instead of propionic anhydride, the following two compounds, isolated as their hydrochlorides, have been prepared:

4-[1″-acetoxy-2″-(N-imidazolyl)-ethyl]-biphenyl hydrochloride (15/1560)

(Iaiii: n=0, R, R$_1$ and R$_2$ are H, H$_3$ is acetoxy, R$_4$ is 4-biphenylyl) M.P. 214°–7° C.

4-[1″-butyryloxy-2″-(N-imidazolyl)-ethyl]-biphenyl hydrochloride (15/1564)

(Iaiii: n-0, R, R$_1$ and R$_2$ are H, R$_3$ is butyryloxyy, R$_4$ is 4-biphenylyl) M.P. 170° C.

EXAMPLE 21

4-(N-imidazolyl-vinylene)-biphenyl (15/1598)

(Ic: n=0, R$_4$ is 4-biphenylyly)

A mixture consisting of 2.64 g of 4-[1″-hydroxy-2″-(N-imidazolyl)-ethyl]-biphenyl, prepared as described in Example 16 and 26 ml of concentrated hydrochloric acid, was refluxed 24 hours. At the end of the reaction, the mixture was cooled at room temperature, diluted with water and sodium hydroxide was added. The desired product separated as an oil, was extracted with chloroform and the solvent was evaporated off. After purification by silica gel column chromatography, using first benzene and then benzene/acetone (9/1) as eluant, 0.79 g of pure product were obtained. M.P. 174°–6° C.

| Analysis for C$_{17}$H$_{14}$N$_2$ | C % | H % | N % |
|---|---|---|---|
| Calculated | 82.90 | 5.73 | 11.37 |
| Found | 82.60 | 5.74 | 11.33 |

EXAMPLE 22

4-[2''-(N-imidazolyl)-ethyl]-biphenyl hydrochloride (15/1625)

(Iaii: n=0, R4=4-biphenylyl)

To a solution of 2.46 g of 4-(N-imidazolyl-vinylene)-biphenyl, prepared as described in Example 21, in 40 ml of ethanol containing 0.01 mole of hydrogen chloride in ethanol, 0.2 g of 10% palladium on carbon were added and the suspension was hydrogenated at room temperature and atmospheric pressure. When the hydrogen absorption was over, the catalyst was washed with methanol and the solution evaporated to dryness in vacuo. After several crystallizations from isopropanol, 1.7 g of the title compound were obtained. M.P. 168°–9° C.

| Analysis for $C_{17}H_{16}N_2HCL$ | | | | |
|---|---|---|---|---|
| | C % | H % | N % | Cl % |
| Calculated | 71.70 | 6.02 | 9.83 | 12.45 |
| Found | 71.68 | 6.04 | 9.78 | 12.32 |

EXAMPLE 23

Operating as described in Examples 10 to 18 and 21, and starting from known substances or from the intermediates described in Examples 1 to 9, the compounds listed in Tables II and III were prepared.

TABLE II

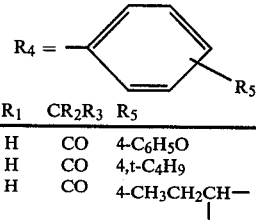

$R_4 = $ (phenyl)–$R_5$

| COMPOUND | n | R | $R_1$ | $CR_2R_3$ | $R_5$ | Mp in °C. | |
|---|---|---|---|---|---|---|---|
| 15/1388 | 0 | H | H | CO | 4-$C_6H_5O$ | 126–127 | |
| 1501 | 0 | H | H | CO | 4,t-$C_4H_9$ | 144–146 | |
| 1502 | 0 | H | H | CO | 4-$CH_3CH_2CH(CH_3)$— | 76–79 | |
| 1493 | 0 | H | H | CO | 2-$C_6H_5$ | 118–119 | |
| 1596 | 1 | H | $CH_3$ | CO | 4-$C_6H_5$ | 160 | |
| 1587 | 0 | $CH_3$ | H | CO | 4,$C_6H_5CH_2CH_2$ | 190–194 | hydrochloride |
| 1588 | 0 | $CH_3$ | $CH_3$ | CO | 4,$C_6H_5CH_2CH_2$ | 91–92 | |
| 1370 | 0 | H | H | CO | 4-$CH_3S$ | 170–171 | |
| 1405 | 0 | H | H | CO | 4-$C_2H_5S$ | 137 | |
| 1377 | 0 | H | H | CO | 4,n-$C_3H_7S$ | 80 | |
| 1443 | 0 | H | H | CO | 4,i-$C_3H_7S$ | 116 | |
| 1379 | 0 | H | H | CO | 4,n-$C_4H_9S$ | 100 | |
| 1444 | 0 | H | H | CO | 4,i-$C_5H_{11}S$ | 82–84 | |
| 1413 | 0 | H | H | CO | 2-$C_6H_5S$ | 118 | |
| 1410 | 0 | H | H | CO | 3-$C_6H_5S$ | 94 | |
| 1352 | 0 | H | H | CO | 4-$C_6H_5S$ | 138–139 | |
| 1527 | 0 | $CH_3$ | H | CO | 4-$C_6H_5S$ | 192–193 | hydrochloride |
| 1528 | 0 | $CH_3$ | $CH_3$ | CO | 4-$C_6H_5S$ | 106–107 | |
| 1555 | 1 | H | H | CHOH | 4-$C_6H_5$ | 144–145 | |
| 1617 | 1 | H | $CH_3$ | CHOH | 4-$C_6H_5$ | 153–156 | |
| 1619 | 0 | $CH_3$ | H | CHOH | 4-$C_6H_5CH_2CH_2$ | 116–117 | |
| 15/1620 | 0 | $CH_3$ | $CH_3$ | CHOH | 4-$C_6H_5CH_2CH_2$ | 125–127 | |
| 1624 | 1 | H | H | CHOH | 4-$C_6H_5CH_2CH_2$ | 148–149 | |
| 1404 | 0 | H | H | CHOH | 4-$CH_3S$ | 179–181 | |
| 1391 | 0 | H | H | CHOH | 4-$C_2H_5S$ | 140 | |
| 1375 | 0 | H | H | CHOH | 4,n-$C_3H_7S$ | 142 | |
| 1442 | 0 | H | H | CHOH | 4,i-$C_3H_7S$ | 140 | |
| 1374 | 0 | H | H | CHOH | 4,n-$C_4H_9$ | 136 | |
| 1455 | 0 | H | H | CHOH | 4,i-$C_5H_{11}S$ | 141 | |
| 1434 | 0 | H | H | CHOH | 2-$C_6H_5S$ | 102 | |
| 1411 | 0 | H | H | CHOH | 3-$C_6H_5S$ | 166 | hydrochloride |
| 1343 | 0 | H | H | CHOH | 4-$C_6H_5S$ | 116–117 | |
| 1540 | 0 | $CH_3$ | H | CHOH | 4-$C_6H_5S$ | 145 | |
| 1541 | 0 | $CH_3$ | $CH_3$ | CHOH | 4-$C_6H_5S$ | 115 | |
| 1402 | 0 | H | H | CHOH | 4-$C_6H_5O$ | 160–162 | |
| 1504 | 0 | H | H | CHOH | 4,t-$C_4H_9$ | 113–115 | |
| 1505 | 0 | H | H | CHOH | 4-$CH_3CH_2CH(CH_3)$— | 124 | |
| 1508 | 0 | H | H | CHOH | 2-$C_6H_5$ | 227–230 | hydrochloride |
| 1428 | 0 | H | H | CHOH | 3-$C_6H_5$ | 144–145 | " |
| 1401 | 0 | $CH_3$ | H | CHOH | 4-$C_6H_5$ | 190–192 | |
| 1492 | 0 | $CH_3$ | $CH_3$ | CHOH | 4-$C_6H_5$ | 212 | |
| 1584 | 0 | —CH=CH— | | | 4-$C_6H_5S$ | 108–109 | |
| 1456 | 0 | $C_6H_3$ | H | CO | H | 127 | nitrate |
| 15/1489 | 0 | $C_6H_5$ | H | CO | 4$C_6H_5$ | 234–235 | hydrochloride |
| 1537 | 0 | $C_6H_5$ | H | CO | 4$C_6H_5S$ | 228 | " |
| 1440 | 0 | H | H | CO | 4$C_6H_5CH_2S$ | 164 | |
| 1498 | 0 | H | H | CO | 4OH | 249–251 | hydrochloride |
| 1499 | 0 | H | H | CO | 3,4(OH)$_2$ | 253–254 | " |
| 1500 | 0 | H | H | CO | 4$NH_2$ | 201–207 | |
| 1449 | 0 | H | H | CO | 4$CH_2CONH$ | 231–233 | |
| 1420 | 0 | H | H | CO | 4$NO_2$ | 164–168 | |
| 1439 | 0 | $C_6H_5$ | H | CHOH | H | 166 | |

TABLE II,-continued
$$R_4 = \text{—}\underset{R_5}{\text{C}_6\text{H}_4}\text{—}$$
| COMPOUND | n | R | $R_1$ | $CR_2R_3$ | $R_5$ | Mp in °C. | |
|---|---|---|---|---|---|---|---|
| 1491 | 0 | $C_6H_5$ | H | CHOH | $4C_6H_5$ | 213–216 | |
| 1549 | 0 | H | H | CHOH | 4-OH | 184–185 | |
| 1623 | 0 | H | H | CHOH | 3,4(OH)$_2$ | 264–267 | hydrochloride |
| 1551 | 0 | H | H | CHOH | 4NH$_2$ | 175–178 | " |
| 1448 | 0 | H | H | CHOH | 4NO$_2$ | 188–189 | |
| 1600 | 0 | H | H | CHOH | 4-i.C$_5$H$_{11}$ | | |
TABLE III
| COMPOUND | n | R | $R_1$ | $CR_2R_3$ | $R_4$ | Mp in °C. |
|---|---|---|---|---|---|---|
| 15/1450 | 0 | H | H | CO | 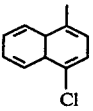 | 145–147 |
| 1432 | 0 | H | H | CHOH | 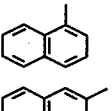 | 250 hydrochloride |
| 1423 | 0 | H | H | CO | 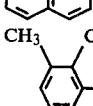 | 129 |
| 1650 | 0 | CH$_3$ | H | CO | 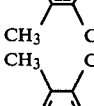 | 124 |
| 1640 | 0 | CH$_3$ | CH$_3$ | CO | 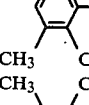 | 105–106 |
| 1565 | 1 | H | H | CO | 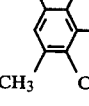 | 126–127 |
| 1452 | 0 | H | H | CHOH | 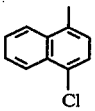 | 242–243 hydrochloride |
| 1424 | 0 | H | H | CHOH | 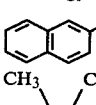 | 157–158 |
| 1340 | 0 | H | H | CHOH | 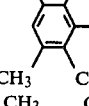 | 230–232 |
| 1458 | 0 | H | H | CHOH | 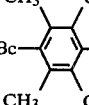 | 228–230 |
| 15/1454 | 0 | H | H | CHOH | 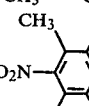 | 220–221 |
| 1562 | 0 | nC$_3$H$_7$ | H | CO | 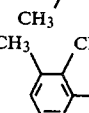 | 122 |

TABLE III-continued

| COMPOUND | n | R | R₁ | CR₂R₃ | R₄ | Mp in °C. |
|---|---|---|---|---|---|---|
| 1451 | 0 | H | H | CO | tetrahydronaphthyl | 152 |
| 1453 | 0 | H | H | CHOH | tetrahydronaphthyl | 115–116 |

Although the invention has been described in detail for the purposes of illustration, it is to be understood that such detail is solely for the purpose of illustration and that variations can be made therein without departing from the spirit and scope of the invention except as it may be limited by the claims.

What is claimed is:

1. An imidazole derivative of the general formula $$R_4-\underset{\underset{R_3}{|}}{\overset{\overset{R_2}{|}}{C}}-\underset{\underset{R_1}{|}}{\overset{\overset{R}{|}}{C}}-(CH_2)_n-N\underset{\diagdown}{\diagup}\overset{H}{\underset{C}{\overset{C\diagdown}{\underset{\diagup}{\phantom{X}}}}N}\underset{H}{\overset{\phantom{X}}{\underset{\phantom{X}}{\phantom{X}}}}CH$$

wherein $R_4$ represents a 1,2,3,4-tetrahydro-6-naphthyl group or a phenyl group substituted in the 4-position by a phenyl, cyclohexyl, or phenylthio group, a 4-bibenzyl group or a 3,4-dihydroxy-phenyl group, n is 0, 1 or 2, and (a) each of R and $R_1$, which may be the same or different represents a hydrogen atom, an alkyl group having from 1 to 6 carbon atoms or a phenyl group, R or $R_1$ being a phenyl group when $R_4$ is biphenyl, one of $R_2$ and $R_3$ represents a hydrogen atom, and the other of $R_2$ and $R_3$ represents a hydroxyl group, $R_2$—C—$R_3$ being carbonyl when $R_4$ is 3,4 dihydroxy phenyl, (b) n, $R_4$, R and $R_1$ are as defined in (a) and $R_2$ and $R_3$ together represent an oxygen atom, except when $R_4$ is phenyl substituted by 4-phenylthio, or $$-\underset{\underset{R_3}{|}}{\overset{\overset{R_2}{|}}{C}}-\underset{\underset{R_1}{|}}{\overset{\overset{R}{|}}{C}}- \quad (c)$$

represents a vinylene group and
$R_4$ and n are the same as above, or
a pharamceutically acceptable acid addition salt thereof.

2. The product of claim 1 wherein the formula represents 1-(N-imidazolyl-acetyl)-4-cyclohexyl-benzene.

3. The product of claim 1 wherein the formula represents 4-[3″-(N-imidazolyl)-propionyl]-bibenzyl.

4. The product of claim 1 wherein the formula represents 4-(N-imidazolyl-acetyl)-bibenzyl.

5. The product of claim 1 wherein the formula represents 1-[1′-hydroxy-2′-(N-imidazolyl)-ethyl]-4-cyclohexylbenzene.

6. The product of claim 1 wherein the formula represents 4-[1″-hydroxy-2″-(N-imidazolyl)-ethyl]-bibenzyl.

7. The product of claim 1 wherein the formula represents 4-[2″-(N-imidazolyl)-propionyl]-bibenzyl hydrochloride.

8. The product of claim 1 wherein the formula represents 4-[2″-methyl-2″-(N-imidazolyl)-propionyl]-bibenzyl.

9. The product of claim 1 wherein the formula represents 4-[1″-hydroxy-2″-(N-imidazolyl)-propyl]-bibenzyl.

10. The product of claim 1 wherein the formula represents 4-[1″-hydroxy-2″-methyl-2″-(N-imidazolyl)-propyl]-bibenzyl.

11. The product of claim 1 wherein the formula represents 4-[1″-hydroxy-3″-(N-imidazolyl)-propyl]-bibenzyl.

12. The product of claim 1 wherein the formula represents 1-(N-imidazolyl-vinylene)-4-phenylthio-benzene.

13. The product of claim 1 wherein the formula represents α-(N-imidazolyl)-benzyl 4-biphenylyl ketone hydrochloride.

14. The product of claim 1 wherein the formula represents 4-(N-imidazolyl-acetyl)-catechol hydrochloride.

15. The product of claim 1 wherein the formula represents 4-phenyl-α-hydroxy-β-(N-imidazolyl)-bibenzyl.

16. The product of claim 1 wherein the formula represents 1,2,3,4-tetrahydro-6-(N-imidazolyl-acetyl)-naphthalene.

17. The product of claim 1 wherein the formula represents 1,2,3,4-tetrahydro-6-[1′-hydroxy-2′-(N-imidazolyl)-ethylnaphthalene.

18. An anticonvulsant composition which comprises a pharmaceutically acceptable diluent or carrier and, as active ingredient, an effective amount of an imidazole derivative as claimed in claim 1, 2, 3, 4, 5, 6, 7, 8, 48–50, 69, 71, 75, 80, 98, or 99.

19. An anticonvulsant composition according to claim 18, wherein the effective amount of the imidazole derivative of claim 1, is between 50 and 700 mg.

* * * * *

UNITED STATES PATENT AND TRADEMARK OFFICE
CERTIFICATE OF CORRECTION

PATENT NO. : 4,275,071

DATED : June 23, 1981

INVENTOR(S) : Dante Nardi; Alberto Tajano; Maria J. Magistretti

It is certified that error appears in the above-identified patent and that said Letters Patent are hereby corrected as shown below:

On the title page, Item [75],
in the listing of Inventors: "Alberto Tajano" should read -- Alberto Tajana -- column 2, line 22: "n-1" should read -- n=1 --

Claim 18, lines 4 and 5: "claim 1, 2, 3, 4, 5, 6, 7, 8, 48-50, 69, 71, 75, 80, 98, or 99." should read -- claim 1, 2, 3, 4, 5, 6, 7, 8, 9-11, 12, 13, 14, 15, 16, or 17.

Signed and Sealed this

Twentieth Day of April 1982

[SEAL]

*Attest:*

*Attesting Officer*

GERALD J. MOSSINGHOFF

*Commissioner of Patents and Trademarks*